(12) United States Patent
Sasaki et al.

(10) Patent No.: US 7,711,091 B2
(45) Date of Patent: May 4, 2010

(54) X-RAY ANALYSIS APPARATUS

(75) Inventors: Akito Sasaki, Akishima (JP); Aya Kuribayashi, Akishima (JP); Keiichi Morikawa, Fuchu (JP); Kunio Nishi, Hachioji (JP); Takao Ohara, Higashimurayama (JP); Toshiyuki Kato, Akishima (JP); Yuji Tsuji, Hamura (JP)

(73) Assignee: Rigaku Corporation, Tokyo (JP)

( * ) Notice: Subject to any disclaimer, the term of this patent is extended or adjusted under 35 U.S.C. 154(b) by 185 days.

(21) Appl. No.: 11/880,638

(22) Filed: Jul. 23, 2007

(65) Prior Publication Data

US 2008/0056452 A1 Mar. 6, 2008

(30) Foreign Application Priority Data

Aug. 29, 2006 (JP) .............................. 2006-231728

(51) Int. Cl.
*H05G 1/58* (2006.01)
*H05G 1/00* (2006.01)

(52) U.S. Cl. ........................ 378/116; 378/115; 378/210

(58) Field of Classification Search ................... 378/70, 378/71, 114–116, 204, 205, 210
See application file for complete search history.

(56) References Cited

U.S. PATENT DOCUMENTS

2003/0194056 A1* 10/2003 Spahn ........................ 378/205

2007/0165783 A1* 7/2007 Abu Tabanjeh ............. 378/116

FOREIGN PATENT DOCUMENTS

| JP | 6-74923 A | 3/1994 |
| JP | 8-155045 A | 6/1996 |

OTHER PUBLICATIONS

Materials Analytical Sciences (MAS), X-ray Diffraction / X-ray Reflectivity (XRD/XRR), Press Release 2004, pp. 1-3.*
SmartLab Product Brochure, Rigaku 2005, pp. 1-8.*
Gregory Roumeliotis, LabTechnologist.com, PANalytical revamps its diffractometer, Press Release Feb. 22, 2006, pp. 1-2.*
Ultima IV Product Brochure, Rigaku Jan. 8, 2007, pp. 1-13.*

* cited by examiner

*Primary Examiner*—Edward J Glick
*Assistant Examiner*—Anastasia Midkiff
(74) *Attorney, Agent, or Firm*—Frishauf, Holtz, Goodman & Chick, P.C.

(57) ABSTRACT

An X-ray analysis apparatus has information about a relationship between selection of a measurement type and a replacement work of optical parts and shows, on a screen of a display, graphical information about optical parts which should be changed, to make it easy for an operator to perform a preliminary work before measurement. When the operator selects one desired measurement type among a plurality of measurement types in a selection window, there is displayed on the display, depending on the selected measurement type, graphical information about necessary optical parts which should be newly installed and/or installed optical parts which should be removed. The operator looks at the operating instructions and then performs the replacement work. The graphical information may be: graphical indication of the installation locations of the optical parts; different pictorial expressions about the installation and the removal works; and graphical indication of the identification marks of the optical parts.

14 Claims, 21 Drawing Sheets

FIG. 2

| Category | Installation location | Type of optical part | Type of sensor |
|---|---|---|---|
| CBO selection slit | | [Without unit] | Photosensor |
| | CBO unit | [Without selection slit]<br>Selection slit BB<br>Selection slit PB<br>Selection slit SA<br>Selection slit MA | |
| Incident optical device | — | [Without monochromator] | Connector |
| | — | 2-bounce monochromator Ge(220)x2<br>2-bounce monochromator Ge(400)x2 | |
| | — | 4-bounce monochromator Ge(220)x4<br>4-bounce monochromator Ge(440)x4 | |
| Incident parallel slit | 2-bounce monochromator or Incident parallel slit adaptor | [Without adaptor]<br>[Without slit]<br>Soller slit open<br>Soller slit 5.0 deg<br>Soller slit 2.5 deg<br>In-plane PSC 1.0 deg<br>In-plane PSC 0.5 deg<br>In-plane PSC 0.15 deg | Photosensor |
| Length limiting slit | Incident slit box | [Without length limiting slit]<br>Length limiting slit 0.5 (mm)<br>Length limiting slit 2 (mm)<br>Length limiting slit 5 (mm)<br>Length limiting slit 10 (mm)<br>Length limiting slit 15 (mm) | Photosensor |

FIG. 3

| Category | Installation location | Type of optical part | Type of sensor |
|---|---|---|---|
| Filter | Receiving slit box | [Without filter]<br>CuKβ filter | Microswitch |
| Receiving optical device | — | [Without analyzer/adaptor] | |
| | — | 2-bounce analyzer Ge(220)x2<br>2-bounce analyzer Ge(400)x2 | Connector |
| | Receiving optical device adaptor | [Without PSA]<br>PSA open<br>PSA 1.0 deg<br>PSA 0.5 deg<br>PSA 0.114 deg<br>PSA 0.05 deg<br>Vacuum path | Photosensor |
| Receiving parallel slit | Receiving parallel slit adaptor | [Without adaptor]<br>[Without slit]<br>Soller slit 5.0 deg<br>Soller slit 2.5 deg<br>In-plane PSA 1.0 deg<br>In-plane PSA 0.5 deg<br>In-plane PSA 0.114 deg | Photosensor |
| Diffracted beam monochromator | Dector adaptor | [Without unit]<br>[Without diffracted beam monochromator unit]<br>Diffracted beam monochromator Bent<br>Diffracted beam monochromator Flat | Connector and Microswitch |
| Monochromator slit | Diffracted beam monochromator unit | [Without monochromator]<br>Monochromator slit BBM | Microswitch |

FIG. 6

| Optics Alignment (BB) | ☒ |

Change optics

Current attribute: Medium-resolution parallel beam/RS

Destination attribute: Bragg-Brentano focusing

Optics alignment conditions

☐ Change optics without adjustment

Optics alignment Name  [@BB focusing ▼]

☐ Print out results after alignment

[?]

[Execute] [Import...] [Export...] [OK] [Cancel]

FIG. 7

| Sample Alignment (BB) | ☒ |

Sample alignment conditions

○ Use the height reference sample plate (no height alignment)

○ Curved sample (Z scan only)

⦿ Flat sample

Sample thickness (mm) [3.0]

⦿ Run recommended sequence    ○ Customize conditions    [Customize...]

☑ Put a sample when the sample alignment starts.

☐ Put a sample every time the sample alignment starts in a repeated measurement.

☐ Print alignment result    [?]

[Execute] [Import...] [Export...] [OK] [Cancel]

FIG. 8

| Quick Theta/2-Theta Meas. (BB) | ☒ |

Save measured data

File name: C:¥Documents and Settings¥Administrator¥....
Sample name:
Memo:

Quick Theta/2-Theta measurement conditions

Sample: [Inorganic ▼]

Step      ○ Fine        ⊙ Standard      ○ Coarse
Speed     ○ Slow        ⊙ Standard      ○ Fast Monochromatization
          ⊙ K beta filter         ○ Diffracted beam
             method                  monochromator method ⊙ Run recommended    ○ Customize       [Customize...]
   sequence             conditions Calculated scan duration: 00:21:45         [?]

[Execute] [Import...] [Export...] [OK] [Cancel]

FIG. 9

| Optics Alignment (PB) | ☒ |

Change optics

Current attribute: Bragg-Brentano focusing

Destination attribute: Medium resolution parallel beam/RS

Optics alignment condition

☐ Change optics

Optics alignment name: @Medium resolution PB ▼

☐ Alignment for in-plane measurement

☐ Print out results after alignment

[ ? ]

[Execute] [Import...] [Export...] [OK] [Cancel]

FIG. 10

| Sample alignment | ☒ |

Sample information

☑ Direct beam half cut alignment conditions

Sample thickness (mm) [1.0]

☑ Surface normal alignment conditions

Sample width (mm) [10.0]

Alignment criteria
[Standard ▼]

Sample height (mm) [10.0]

Surface density
[Medium ▼]

☑ Clear omega offset   ☑ Set chi, phi = 0

⦿ Run recommended sequence   ◯ Customize conditions   [Customize...]

☑ Put a sample when the sample alignment starts.

☐ Put a sample every time the sample alignment starts in a repeated measurement.

[?]

[Execute] [Import...] [Export...] [OK] [Cancel]

FIG. 11

| Reflectivity Measurement | ☒ |

Save data

File name: C:¥Documents and Settings¥Administrator¥....

Sample name:

Memo:

Requested scan duration

Pre-measurement  2.0  min    Data measurement  15.0  min

Return to default values

⦿ Run recommended sequence    ◯ Customize conditions    Customize...

Calculated scan duration: 00:17:00    ?

Execute | Import... | Export... | OK | Cancel

FIG. 12A

| | | CBO selection slit | Incident optical device | Incident parallel slit | Length limiting slit | Filter |
|---|---|---|---|---|---|---|
| Quick θ/2θ measurement (Bragg-Brentano focusing) Sample: Powder with which a glass sample-plate is filled | Optics alignment | BB | None | Soller slit 5.0 deg | 10 mm | None |
| | Sample alignment | | | | | |
| | Data measurement | | | | | |
| Reflectivity measurement (high resolution PB-Ge(220) x2) Sample: Thin film with a size of 1 cm x 1 cm | Optics alignment | PB | Ge(220) x2 | Soller slit open | 10 mm | None |
| | Sample alignment | | | | 5 mm | |
| | Data measurement | | | | | |
| Transmission SAXS measurement Sample: Nano particles encapsulated in a capillary | Optics alignment | SA | None | Soller slit 5.0 deg | 10 mm | None |
| | Sample alignment | | | | | |
| | Data measurement | | | | | |

FIG. 12B

| | | Receiving optical device | Receiving parallel slit | Diffracted beam monochromator | Monochromator slit |
|---|---|---|---|---|---|
| Quick θ/2θ measurement (Bragg-Brentano focusing) | Optics alignment | PSA open | Soller slit 5.0 deg | Bent (with DBM unit) | BBM |
| Sample: Powder with which a glass sample-plate is filled | Sample alignment | | | | |
| | Data measurement | | | | |
| Reflectivity measurement (high resolution PB-Ge(220)x2) | Optics alignment | PSA open | Soller slit open | None (detector only) | None |
| Sample: Thin film with a size of 1 cm x 1 cm | Sample alignment | | | | |
| | Data measurement | | | | |
| Transmission SAXS measurement | Optics alignment | Vacuum path | None | None (detector only) | None |
| Sample: Nano particles encapsulated in a capillary | Sample alignment | | | | |
| | Data measurement | | | | |

FIG. 13

Prepare to change optical parts when instructed.

CBO selection slit

Incident optical device

Incident parallel slit

Length limiting slit

Diffracted beam monochromator

Monochromator slit

Change optical parts according to the instructions which are displayed in the middle of the measurement prosecution.

OK          Stop

FIG. 14A
Place the height reference sample plate on the attachment.
height reference sample-plate
Insert selection slit PB in CBO unit.
    -> Selection slit BB is currently on CBO unit.
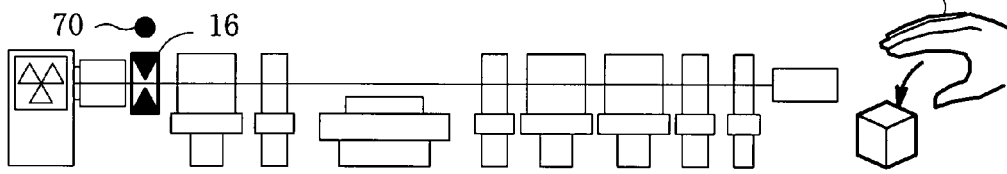
Remove IPS adaptor.
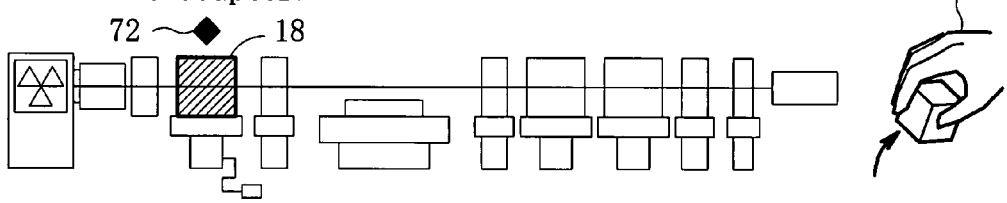
Install 2-bounce monochromator Ge(220)x2 in diffractometer.
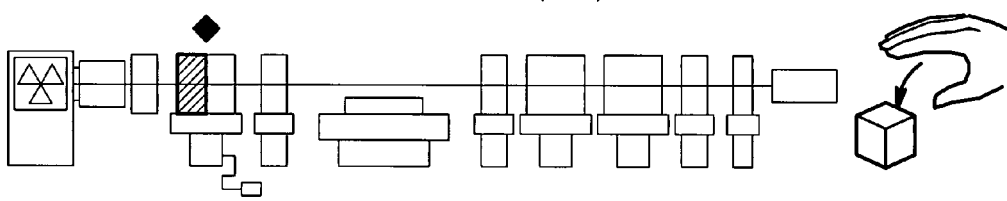
Install Soller-slit-open in 2-bounce monochromator.
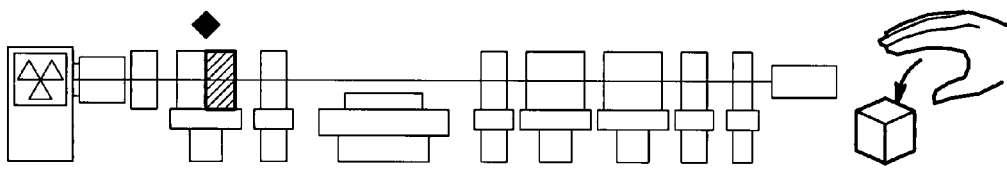

FIG. 16
Place the sample spacer (0-3 mm) and the wafer sample plate (standard) on the attachment.
Place the sample on the wafer sample plate.
 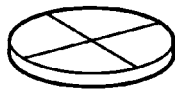 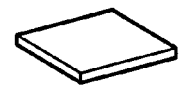
sample spacer     wafer sample plate     wafer sample
Insert length limiting slit 5 (mm) in incident slit box.
   -> Length limiting slit 10 (mm) is currently on incident slit box.
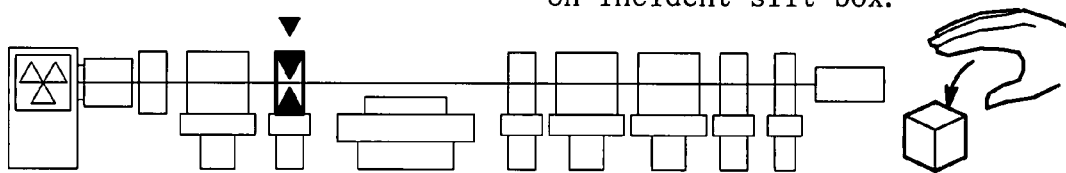
OK            Stop

FIG. 19

| Execute alignment | | | | | | |
|---|---|---|---|---|---|---|
| | Execute | Start | Stop | Sampling step | Scan speed | Delta angle |
| Z | ☑ | -1.5000 mm | 0.5000 mm | 0.0100 mm | 4.0000 mm/min | -0.5000 mm |
| Omega | ☑ | -1.5000 deg | 1.5000 deg | 0.0100 deg | 4.0000 deg/min | -0.5000 deg |

Attenuator: Open   Threshold: 2000 cps   Peak search mode: Peak-top   Number of cycles: 1

| Specimen alignment at 2Theta = 0 | | | | | | | |
|---|---|---|---|---|---|---|---|
| | Execute | -del start | +del stop | Sampling step | Scan speed | Delta angle | Scan order |
| Z | ☑ | -1.5 mm | 0.5 mm | 0.005 mm | 2.0 mm/min | | ⦿ Omega->Z |
| Omega | ☑ | -1.5 deg | 1.5 deg | 0.005 deg | 2.0 deg/min | | ○ Z->Omega |
| | | Start | Stop | | | | ○ Omega |
| Chi | ☐ | -1.0 deg | 1.5000 deg | 0.05 deg | 2.0 deg/min | -1.0 deg | ○ Z |

Attenuator: Open   Threshold: 2000 cps   Peak search mode: Peak-top   2Th./Ome. position: 0.4000 deg   Number of cycles: 1

Automatic condition   Thickness: 1.0 mm   Slit width: 0.2 mm   Save as...   Set

☑ Set Omega to the half of 2Theta   Update

X-RAY ANALYSIS APPARATUS

BACKGROUND OF THE INVENTION

The present invention relates to an X-ray analysis apparatus making it easy for an operator to perform a preliminary work before measurement.

X-ray diffraction measurement of a sample requires a setup operation about the measuring conditions. The setup operation is, however, difficult for an operator inexperienced in the X-ray diffraction measurement. FIG. 19 shows one example of the condition-setup window on the display screen of the conventional X-ray diffraction apparatus. As seen in the window, there are many setup items, and thus it is troublesome for an operator to select proper conditions and/or enter appropriate values for the respective items.

There is known an X-ray diffraction qualitative analysis apparatus making it easier to perform the condition-setup operation, such apparatus being disclosed in Japanese Patent Publication No. 6-74923 A (1994), which will be referred to as the first publication hereinafter.

The X-ray diffraction qualitative analysis apparatus disclosed in the first publication displays a question about the measuring circumstances on a screen, and receives an answer from an operator, and then deduces the measuring conditions in accordance with the knowledge base, so that anybody can easily set the measuring conditions.

Setup of the measuring conditions often requires an operator's work of replacing one or more optical parts. In such a case, if the apparatus in itself can recognize the status of the installed optical parts, the apparatus would be able to notify an operator of information about the installed optical parts. The prior art relating to such notification is also known and disclosed in Japanese Patent Publication No. 8-155045 A (1996) (the second publication). The second publication discloses a radiotherapy apparatus which can recognize the type of the collimator installed in the apparatus.

The radiotherapy apparatus disclosed in the second publication prepares a plurality of collimators with different types. When an operator selects a collimator and installs it on the holder, the operator can look at, from the outside of the holder, what the installed collimator is. Furthermore, the apparatus acquires information about the type of the collimator with the use of a photosensor. In accordance with such information, the built-in computer of the apparatus determines whether the installed collimator is proper or not. If a wrong collimator is installed, the apparatus gives an alarm.

The problem which should be solved by the present invention is as follows. The X-ray diffraction qualitative analysis apparatus disclosed in the first publication has a function of guidance for the setup of the measuring conditions, but the first publication does not mention a replacement work of the optical parts. The X-ray diffraction apparatus is for the qualitative analysis only, and thus it is presumed that the setup of the measuring conditions is possible without replacement of the optical part. That is to say, the divergence slit, the scattering slit and the receiving slit are all considered variable slits, and accordingly the widths of the slits may be varied with the measuring conditions. Thus, the first publication does not disclose a relationship between the replacement work of the optical part and the setup of the measuring conditions, the relationship being used for completing the preliminary work before measurement properly. On the other hand, the radiotherapy apparatus disclosed in the second publication can determine the type of the installed collimator and gives an alarm if necessary, but the second publication does not disclose a relationship between the function of guidance for the measuring conditions and the replacement work of the optical part.

SUMMARY OF THE INVENTION

It is an object of the present invention to provide an X-ray analysis apparatus making it easy for an operator to make a preliminary work before measurement in accordance with a relationship between the selection of the measurement type and the replacement work of the optical parts.

An X-ray analysis apparatus according to the present invention comprises: (a) a main equipment including an optical system for making an X-ray analysis of a sample; (b) a display for displaying information about the main equipment on a screen of the display; (c) selection-window display means for allowing a selection window to be displayed on the display, the selection window being used for selection of one desired measurement type among a plurality of measurement types; (d) measurement type acquisition means for acquiring the measurement type which is selected by an operator in the selection window; (e) a storage for storing a relationship between the measurement type and types of necessary optical parts required for the measurement type in connection with the plurality of the measurement types respectively; (f) sensors for identifying types of installed optical parts which have been installed in the main equipment; and (g) operating instructions means. The operating instructions means is for: acquiring the types of the necessary optical parts corresponding to the measurement type which has been acquired by the measurement type acquisition means in accordance with the relationship which is stored in the storage; comparing the types of the necessary optical parts with the types of the installed optical parts which have been identified by the sensors to recognize one or more mismatched optical parts; and allowing graphical information to be displayed on the display in connection with the mismatched optical parts. The graphical information includes information about: the necessary optical part which should be newly installed in the main equipment; and/or the installed optical part which should be removed from the main equipment.

The operating instructions means preferably i) allows the type of the necessary optical part which should be newly installed in the main equipment and/or the type of the installed optical part which should be removed from the main equipment to be displayed on the display and ii) allows installation locations in optical system of such optical parts to be graphically displayed on the display. Further, the operating instructions means preferably allows an installation work of the necessary optical part and a removal work of the installed optical part to be graphically displayed on the display, the installation and the removal works being depicted with different pictorial expressions. Furthermore, the optical parts to be used in the X-ray analysis apparatus may be classified into a plurality of categories, so that the optical parts can be changed among the optical parts belonging to the same category. Each of the optical parts may have an identification mark which identifies the category to which the optical part should belong. In such a case, the operating instructions means allows the identification mark to be displayed when showing, on the display, the type of the necessary optical part which should be newly installed in the main equipment and/or the type of the installed optical part which should be removed from the main equipment.

The present invention has an advantage described below. When the operator selects the measurement type in the selection window, the operator can easily understand the replacement work of the necessary optical parts which are required for the selected measurement type, because the replacement work of the optical parts is associated with the function of the selection of the measurement type. The operator can perform the replacement work of the optical parts in accordance with the information displayed on the operating instructions window. Especially, the information about the optical parts which should be changed is displayed graphically, and thus the operator can easily understand the installation locations and the types of the optical parts which should be installed. When a wrong optical part is installed mistakenly, operating instructions for a replacement work for the proper optical part are displayed, so that erroneous installation of the optical parts is prevented.

BRIEF DESCRIPTION OF THE DRAWINGS

FIG. 2 shows a table indicating specific optical parts belonging to respective categories in the incident optical system;

FIG. 3 shows a table indicating specific optical parts belonging to respective categories in the receiving optical system;

FIG. 6 shows a setup window for the optics alignment in the quick $\theta/2\theta$ measurement;

FIG. 7 shows a setup window for the sample alignment in the quick $\theta/2\theta$ measurement;

FIG. 8 shows a setup window for the data measurement in the quick $\theta/2\theta$ measurement;

FIG. 9 shows a setup window for the optics alignment in the reflectivity measurement;

FIG. 10 shows a setup window for the sample alignment in the reflectivity measurement;

FIG. 11 shows a setup window for the data measurement in the reflectivity measurement;

FIG. 12A shows a part of a table indicating a relationship between the measurement types and the types of optical part;

FIG. 12B shows the other part of the table indicating a relationship between the measurement types and the types of optical part;

FIG. 13 shows a window for notifying an operator of a replacement work of the optical parts;

FIG. 14A shows the first half of an operating instructions window;

FIG. 16 shows another operating instructions window;

FIG. 19 shows a condition-setup window of the conventional X-ray analysis apparatus.

DETAILED DESCRIPTION OF THE PREFERRED EMBODIMENTS

Figure 1A:
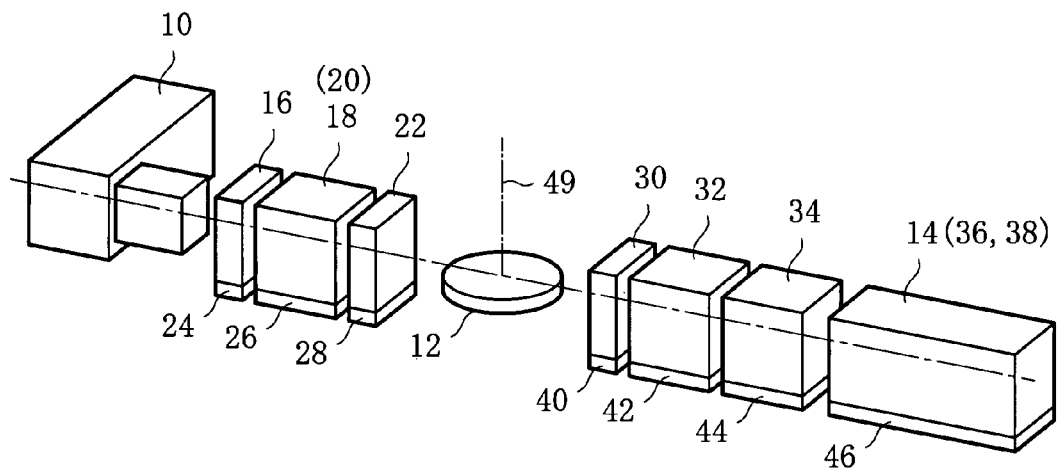
FIGS. 1A and 1B are perspective views each of which illustrates the optics arrangement of one embodiment of the X-ray analysis apparatus according to the present invention.

Embodiments of the present invention will now be described in detail below with reference to the drawings. FIG. 1A is a perspective view schematically illustrating the optics arrangement of one embodiment of the X-ray analysis apparatus according to the present invention. The X-ray analysis apparatus is for analyzing a thin film sample and can make the X-ray diffraction measurement, the X-ray small-angle scattering measurement and the reflectivity measurement. Referring to FIG. 1A, the apparatus has an X-ray tube 10, a sample stage 12 and an X-ray detector 14. Between the X-ray tube 10 and the sample stage 12 are arranged some of the incident optical parts, and between the sample stage 12 and the X-ray detector 14 are arranged some of the receiving optical parts.

The incident optical parts are classified to a plurality of categories: a CBO selection slit 16, an incident optical device 18, an incident parallel slit 20 and a length limiting slit 22. It should be noted that the incident optical device 18 and the incident parallel slit 20 occupy the same installation location. At the respective locations of the categories are installed specific optical parts which belong to the respective categories. Stating in detail, a specific optical part belonging to the CBO selection slit 16 may be installed in a CBO unit 24. A specific optical part belonging to the incident optical device 18 may be installed in an incident optical device base 26. A specific optical part belonging to the incident parallel slit 20 may be installed in a two-bounce monochromator which is one of the optical parts belonging to the incident optical device 18, or may be installed in the incident optical device base 26 through an incident parallel slit adaptor. A specific optical part belonging to the length limiting slit 22 may be installed in an incident slit box 28.

The receiving optical parts are classified to a plurality of categories: a filter 30, a receiving optical device 32, a receiving parallel slit 34, a diffracted beam monochromator 36 and a monochromator slit 38. It should be noted that the diffracted beam monochromator 36 and the monochromator slit 38 are shown at the same location as the X-ray detector 14 in the drawing. Just like the incident side, at the respective locations of the categories are installed specific optical parts which belong to the respective categories. Stating in detail, a specific optical part belonging to the filter 30 may be installed in a receiving slit box 40. A specific optical part belonging to the receiving optical device 32 may be installed directly in a receiving optical device base 42, or may be installed in a receiving main optical base 42 through a receiving optical device adaptor. A specific optical part belonging to the incident parallel slit 34 may be installed in a receiving parallel slit adaptor 44. A specific optical part belonging to the diffracted beam monochromator 36 may be installed in a detector adaptor 46. When the diffracted beam monochromator unit is installed in the detector adaptor 46, a specific optical part belonging to the monochromator slit 38 may be installed in the diffracted beam monochromator unit.

Figure 1B:
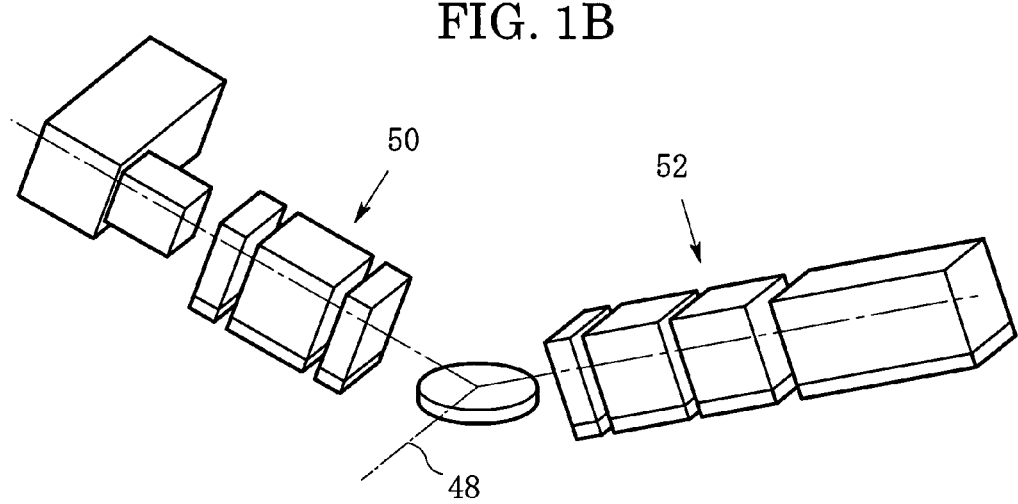

The X-ray analysis apparatus is the horizontal type in which a sample is placed horizontally on the horizontal sample stage 12. Accordingly, when performing the X-ray diffraction $\theta/2\theta$ measurement for example, the incident optical system 50 shown in FIG. 1B rotates around the horizontal axis of rotation 48, while the receiving optical system 52 inversely rotates around the same axis of rotation 48. Additionally, when performing the in-plane diffraction measurement, the receiving optical system in FIG. 1A rotates around the vertical axis of rotation 49.

FIG. 2 shows a table indicating specific optical parts belonging to the respective categories in the incident optical system. Selectable specific optical parts appear in the column "Type of optical part". When one of the optical parts is installed in the apparatus, the type of optical part is identified by a sensor. The column "Type of sensor" of the table indicates the type of such a sensor. A "photosensor" is a reflection photosensor, which will be described later. The photosensor is used for the categories of the CBO selection slit, the incident parallel slit and the length limiting slit. A "connector" is the particular terminal of the connector for electrically connecting the optical part to the apparatus, the particular terminal acting as the sensor for identifying the optical part. A two-bounce monochromator and a four-bounce monochromator each has a signal cable for transmitting a signal between the monochromater and the apparatus, and the connector of the signal cable has the above-described particular terminal used as the sensor. Such a connector sensor is used for the category of the incident optical device.

The CBO selection slit has six options including "without unit" and "without selection slit". Possible selection slits which can be installed in the CBO are four types: selection slits BB, PB, SA and MA. The word CBO is the abbreviation for Cross Beam Optics. The CBO unit makes it easy to select either the Bragg-Brentano focusing method (which uses a diverging X-ray beam coming from the X-ray source as it is) or the parallel beam method (which uses a parallel beam coming from a synthetic parabolic multilayer mirror which transforms the diverging beam to the parallel beam) only with the change of the selection slit. BB is used for the Bragg-Brentano focusing method, PB is used for the parallel beam method, SA is used for the small-angle scattering measurement and MA is used for the micro area measurement. SA is narrower in slit width than PB, and MA is shorter in length than PB.

The incident optical device has five options including "without monochromator". Possible monochromators are four types: two-bounce monochromator Ge(220)×2, two-bounce monochromator Ge(400)×2, four-bounce monochromator Ge(220)×4, and four-bounce monochromator Ge(440)×2.

The incident parallel slit has eight options including "without adaptor" and "without slit". When the two-bounce monochromator has been installed, the optical part belonging to the incident parallel slit can be installed in the monochromator. When the monochromator has not been installed, the incident parallel slit adaptor is first installed in the incident optical device base 26 (see FIG. 1) and thereafter the optical part belonging to the incident parallel slit is installed in the incident parallel slit adaptor. The incident parallel slit is selected among three types of Soller slit and three types of in-plane PSC. The word PSC is the abbreviation for Parallel Slit Collimator.

The length limiting slit has six options including "without length limiting slit". Possible length limiting slits are five types ranging from 0.5 mm to 15 mm.

FIG. 3 shows a table indicating specific optical parts belonging to the respective categories in the receiving optical system. Stating the type of sensor, regarding the receiving optical device in category, the optical parts which should be installed in the receiving optical device adaptor utilize the photosensor. The optical parts belonging to the receiving parallel slit also utilize the photosensor. Regarding the receiving optical device in category again, crystal analyzers utilize the connector as the sensor. Regarding the diffracted beam monochromator in category, the optical parts belonging thereto utilize a combination of the connector and the microswitch. Regarding the filter in category and the monochromator slit in category, the optical parts belonging thereto utilize the microswitch. The microswitch is usable for only the detection of whether or not the optical part is installed, i.e., usable for only the on-off output signal.

The filter has two options: "without filter" and CuKβ filter.

The receiving optical device has ten options including "without analyzer/adaptor". Optical parts which should be directly installed in the receiving optical device base 42 (see FIG. 1A) are a two-bounce analyzer Ge(220)×2 and a two-bounce analyzer Ge(400)×2. Optical parts which should be installed in the receiving optical device base through the receiving optical device adaptor have seven types including "without PSA".

The receiving parallel slit has seven options including "without adaptor" and "without slit". Optical parts belonging to the receiving parallel slit have two types of Soller slit and three types of in-plane PSA. The word PSA is the abbreviation for Parallel Slit Analyzer.

The diffracted beam monochromator has four options including "without unit" and "without diffracted beam monochromator unit". Optical parts belonging to the diffracted beam monochromator are a diffracted beam monochromator Bent and a diffracted beam monochromator Flat.

The monochromator slit has two options: "without monochromator" and monochromator slit BBM.

Figure 4:
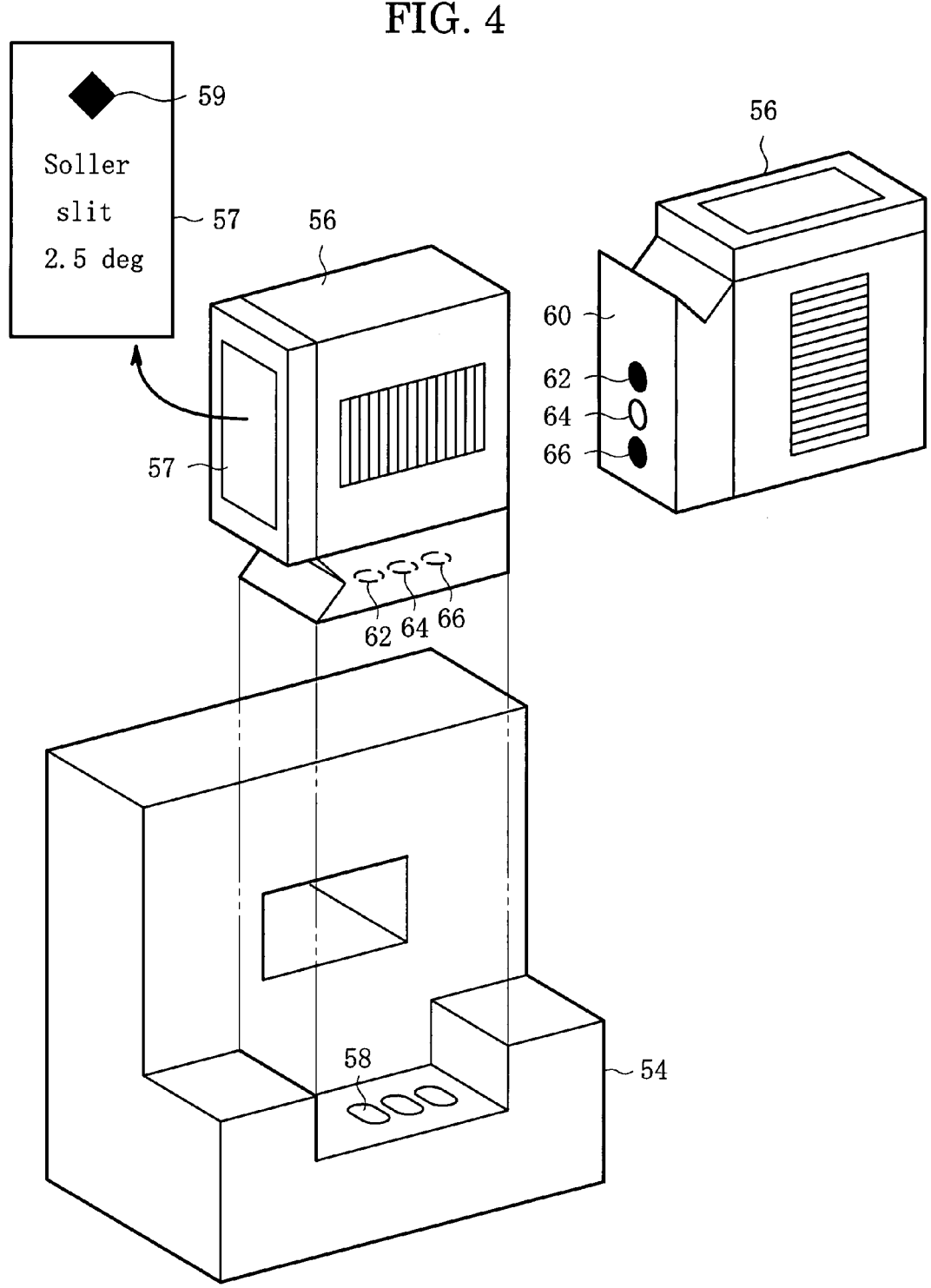
FIG. 4 is a perspective view illustrating a method for identifying the type of optical part with the use of a photosensor.

FIG. 4 is a perspective view illustrating a method for identifying the type of optical part with the use of a photosensor. The drawing depicts the state in which a Soller slit 56 is installed in an incident parallel slit adaptor 54. The incident parallel slit adaptor 54 is provided with three photosensors 58, each of which consists of a combination of a light emitting element and a photo acceptance element. The Soller slit 56 has three indicators 62, 64 and 66 on the bottom surface thereof, one of the indicators being a light reflective area 64 (white) and the other two indicators being light absorbent areas 62 and 66 (black). Each of the photosensors 58 generates an output signal which is the binary signal (one bit) representing whether or not the photosensor receives a reflected light. A combination of the three photosensors generates a three-bit output signal and thus can identify eight types of optical part, the eight being derived from a cube of two. Such a type of photosensor is used for several categories such as the CBO selection slit, the length limiting slit, the receiving optical device and the receiving parallel slit other than the above-described incident parallel slit. In addition, the Soller slit 56 has a skin film 57 affixed thereto, the skin film 57 being provided for identifying the optical part. The skin film 57 has an identification mark 59 and the name of optical part (Soller slit 2.5 deg). The identification mark 57 is for identifying the category to which the optical part belongs. The mark 57 of this example is the specific identification mark (an inclined black square mark) indicating that the optical part belongs to the incident optical device or the incident parallel slit.

Figure 5:
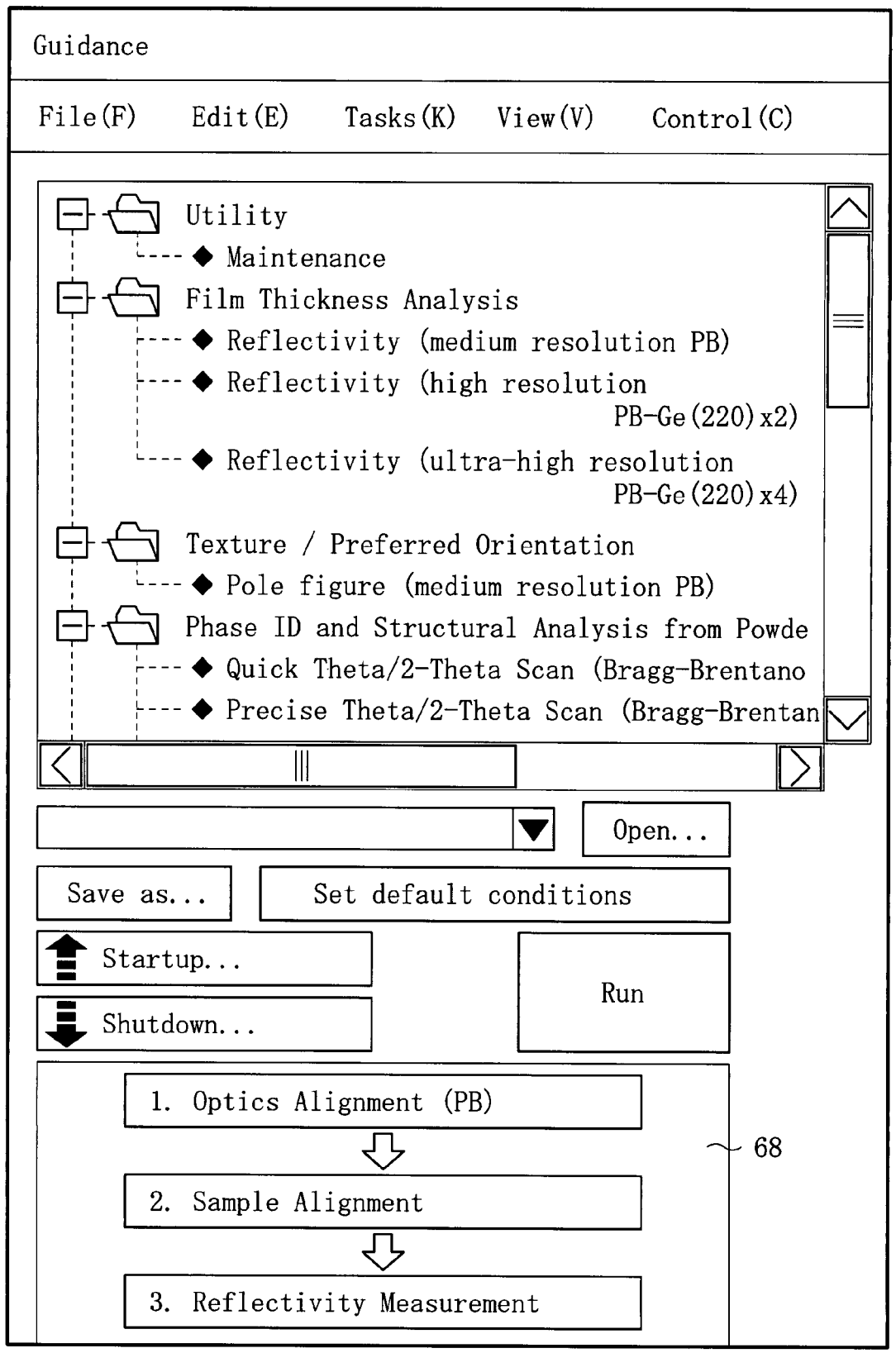
FIG. 5 shows a selection window displayed on the display of the X-ray analysis apparatus.

FIG. 5 shows a selection window displayed on the display of the X-ray analysis apparatus. The selection window shows a plurality of measurement types. The operator can select a desired measurement type. For example in the window, the operator can select, in the Film Thickness Analysis, one of "Reflectivity (medium resolution PB)", "Reflectivity (high resolution PB-Ge(220)×2)" and "Reflectivity (ultra-high resolution PB-Ge(220)×4)". Further, the operator can select, in the Texture/Preferred orientation, "Pole figure (medium resolution PB)". Furthermore, in the Phase ID and Structural Analysis from Powders, "Quick Theta/2-Theta Scan (Bragg-Brentano focusing)" and "Precise Theta/2-Theta Scan (Bragg-Brentano focusing)" can be seen. When the operator clicks a desired measurement type, the measurement type is selected.

The window shown in FIG. 5 has a lower region 68 for indicating three necessary processes for the selected measurement type. The illustrated example indicates the three processes for the selected "Reflectivity (medium resolution PB)": Optics Alignment (PB), Sample Alignment and Reflectivity Measurement. When performing the "Reflectivity (medium resolution PB)", the three processes are required and setup of the measurement conditions is required for the respective processes.

FIGS. 6, 7 and 8 show setup windows for the three processes respectively, i.e., the optics alignment, the sample alignment and the data measurement, in the case that the "Quick Theta/2-Theta Scan (Bragg-Brentano focusing)" is selected as the measurement type. FIG. 6 shows a setup window for the optics alignment, and the operator's work to do in the window is only to confirm the display contents and accordingly there is no item to be set.

FIG. 7 shows a setup window for the sample alignment. The operator sets up the conditions of the sample alignment in the window. Stating in detail, the operator selects whether of not the sample is flat, and if the sample is flat the operator enters the thickness of the sample. Other setting items are automatically set to the standard conditions if the "Run recommended sequence" is selected. The "Run recommended sequence" is the default condition. If the operator wants to set any conditions other than the standard conditions, the operator selects the "Customize conditions" and clicks the "Customize" button to set up desired conditions.

FIG. 8 shows a setup window for the data measurement in the quick θ/2θ measurement (Bragg-Brentano focusing). The operator enters a file name to which the measured data will be saved, and selects the type of the sample. Other setting items are automatically set to the standard conditions if the "Run recommended sequence" is selected.

FIGS. 9, 10 and 11 show setup windows for the three processes respectively, i.e., the optics alignment, the sample alignment and the data measurement, in the case that the "Reflectivity (high resolution PB-Ge(220)×2)" is selected as the measurement type. FIG. 9 shows a setup window for the optics alignment (PB), and the operator's work to do in the window is only to confirm the display contents and accordingly there is no item to be set.

FIG. 10 shows a setup window for the sample alignment, and the operator sets up the conditions of the sample alignment in the window. Stating in detail, the operator enters the sample thickness, the sample width and the sample height. Other setting items are automatically set to the standard conditions if the "Run recommended sequence" is selected.

FIG. 11 shows a setup window for the data measurement in the reflectivity measurement. The operator enters a file name to which the measured data will be saved. Other setting items are automatically set to the standard conditions if the "Run recommended sequence" is selected.

A combination of FIGS. 12A and 12B shows a table indicating a relationship between the measurement types and the types of optical part. The table indicates only three measurement types for example. The "Quick θ/2θ measurement (Bragg-Brentano focusing)" will be first explained. The "Quick θ/2θ measurement (Bragg-Brentano focusing)" is one type of the X-ray diffraction measurement and performs the X-ray diffraction measurement with a relatively wide angular range with the use of the Bragg-Brentano focusing method. A sample to be used is powder with which a glass sample-plate is filled. The same optical parts are used for every the optics alignment, the sample alignment and the data measurement. Stating the optical parts to be used, the selection slit BB is selected as the CBO selection slit; "None" is selected as the incident optical device; the Soller slit 5.0 degrees is selected as the incident parallel slit; the 10 mm is selected as the length limiting slit; "None" is selected as the filter; the PSA open is selected as the receiving optical device; the Soller slit 5.0 degrees is selected as the receiving parallel slit; the Bent is selected as the diffracted beam monochromator; and BBM is selected as the monochromator slit.

Also regarding the "Reflectivity measurement (high resolution PB-Ge(220)×2)" and the "Transmission SAXS measurement", samples to be used and the types of optical part are indicated in FIGS. 12A and 12B. The relationship between the measurement types and the types of optical part as shown in FIGS. 12A and 12B is stored in a storage which is included in the control device of the X-ray analysis apparatus.

Figure 14B:
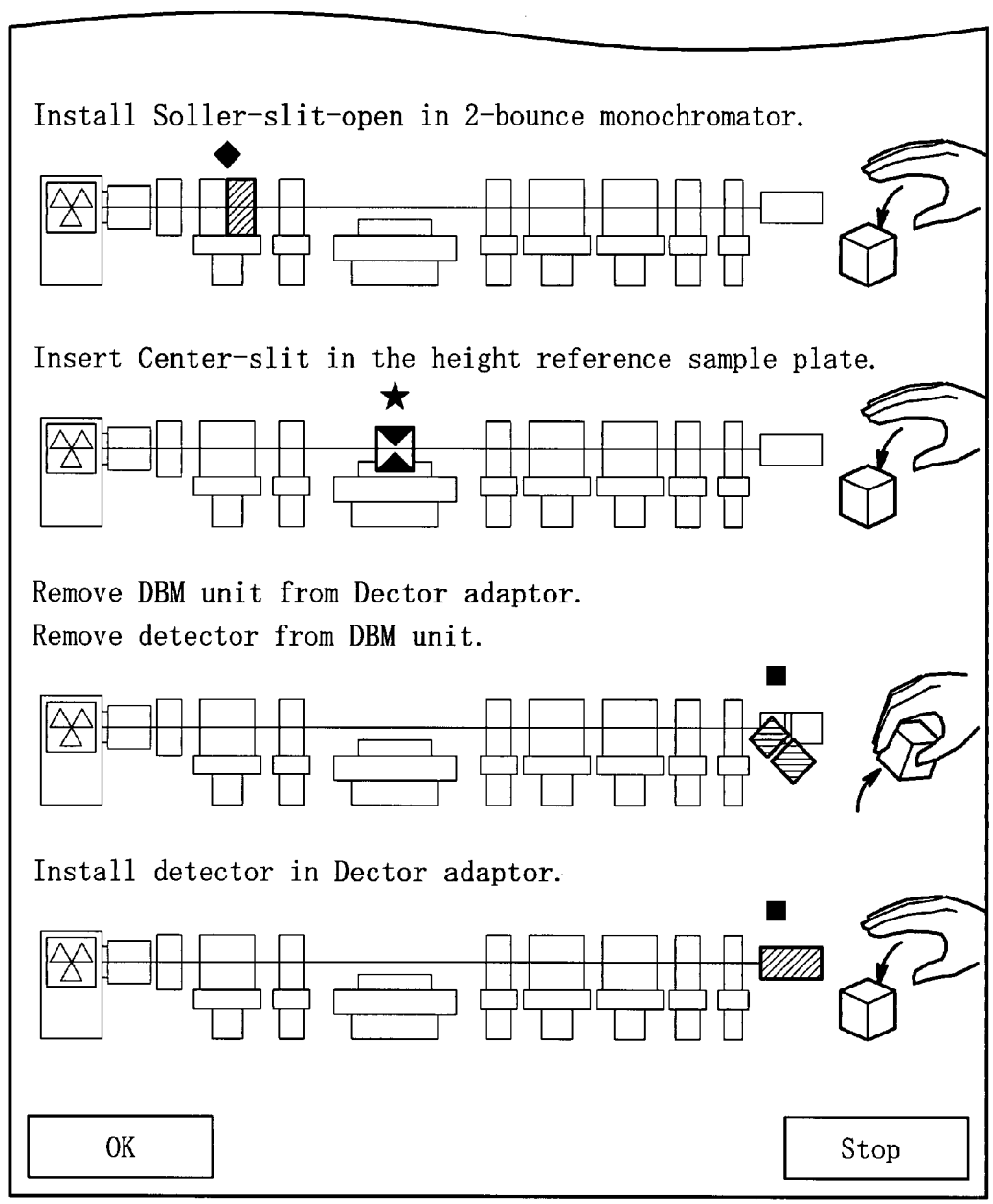
FIG. 14B shows the second half of the operating instructions window.

Next, the total procedure of the preliminary work before measurement will be described with a specific example. It is assumed that the X-ray analysis apparatus has an optical system whose current state is for the "Quick θ/2θ measurement (Bragg-Brentano focusing method)" as shown in the upper part of the table shown in FIGS. 12A and 12B. Then, it is further assumed that the operator wants to perform the "Reflectivity measurement (high resolution PB-Ge(220)×2)" with the use of the same X-ray analysis apparatus. First, the operator opens the selection window shown in FIG. 5 and selects the "Reflectivity (high resolution PB-Ge(220)×2)" in the window. In response to the selection, the lower region 68 shows the three processes for the "Reflectivity (high resolution PB-Ge(220)×2)". When the operator clicks the three process buttons respectively in order, the setup windows shown in FIGS. 9 to 11 open respectively and the operator performs the necessary setup work in the setup windows respectively. Thereafter, the operator clicks the "Run" button. Then, the X-ray analysis apparatus determines the current installation state of the optical parts with the use of the sensors, the current state appearing in the upper part of the table in FIGS. 12A and 12B. The X-ray analysis apparatus next acquires the types of the necessary optical parts required for the reflectivity measurement (high resolution PB-Ge(220)×2) in accordance with the relationship shown in FIGS. 12A and 12B, noting that the acquired types of the optical parts appear in the middle part of the table shown in FIGS. 12A and 12b. Thereafter, the X-ray analysis apparatus compares the current types of the installed optical parts with the types of the necessary optical parts. Comparing them, it is understood that change of the optical part is required for six categories: the CBO selection slit, the incident optical device, the incident parallel slit, the length limiting slit, the diffracted beam monochromator and the monochromator slit. Then, the X-ray analysis apparatus displays a window as shown in FIG. 13. The window is for notifying the operator of the optical parts which should be changed, and the window of this example indicates that the change of the optical part is required for the six categories. When the operator clicks the "OK" button in the window shown in FIG. 13, another operating instructions window opens as shown in FIGS. 14A and 14B, noting that the window is divided into the two drawings.

Figure 15A:
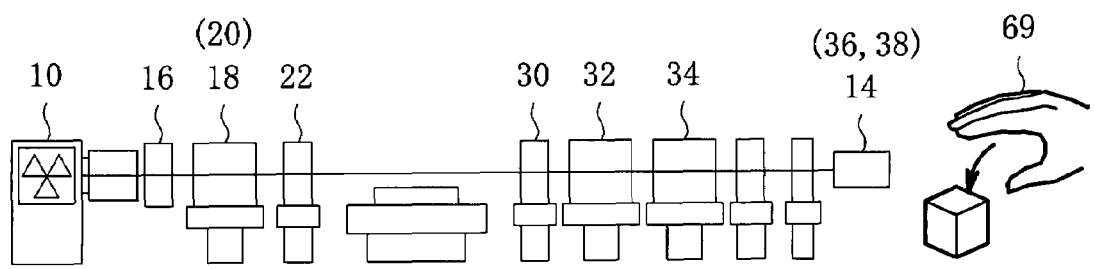
FIGS. 15A to 15C are explanatory views used for explaining how to understand the operating instructions window.

Prior to the explanation of the operating instructions window shown in FIGS. 14A and 14b, there will be described how to understand the operating instructions window with reference to FIGS. 15A to 15C. Referring to FIG. 15A, the graphical expression depicts the respective categories of optical part used in the X-ray analysis apparatus with simplified pictures respectively. Explaining them with referring to FIG. 1A in addition to FIG. 15A, the graphical expression depicts symbolically, as the categories of optical part, the X-ray tube 10, the CBO selection slit 16, the incident optical device 18, the incident parallel slit 20, the length limiting slit 22, the filter 30, the receiving optical device 32, the receiving parallel slit 34, the X-ray detector 14, the counter monochromator 36 and the monochromator slit 38. Further, on the right side of the graphical expression of the optics, there is a pictorial expression 69 which indicates an installation work of the necessary optical part or a removal work of the installed optical part with a different pictorial expression. The pictorial expression of this example has a picture symbolizing a human hand which installs the optical part.

Figure 15B:
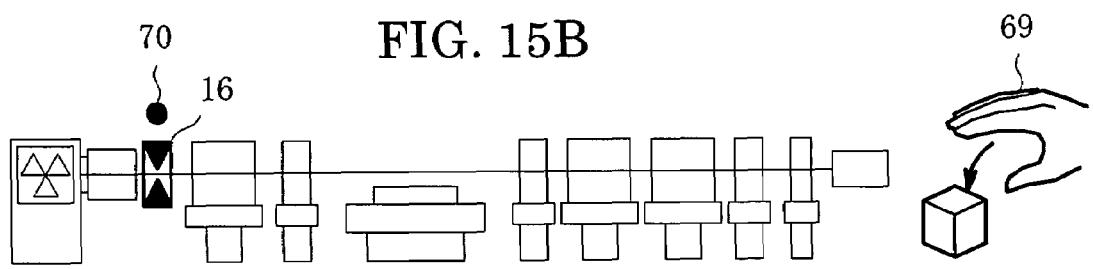

FIG. 15B shows an example indicating how to instruct the installation work. The example indicates the installation of the optical part in the CBO selection slit 16. The category (the CBO selection slit 16) in which the optical part should be installed is highlighted. Further, the identification mark 70 (a black circle mark for the CBO selection slit in this example) peculiar to the category in question appears above the highlighted category. In addition, the specific optical part which should be installed will be indicated with a sentence. After all, the graphic information includes the identification mark (the black circle mark in this example) representing the category of the optical part which should be installed, the installation location (which is highlighted) of the optical part, and the pictorial expression 69 for the installation work. It should be noted that the identification mark 70 (the black circle mark) is prepared in common to the plural optical parts which belong to the CBO selection slit. Accordingly, the operator conveniently makes a search for the necessary optical part among the optical parts having the black circle marks and thus the operator can easily find out the target optical part among many optical parts.

Figure 15C:
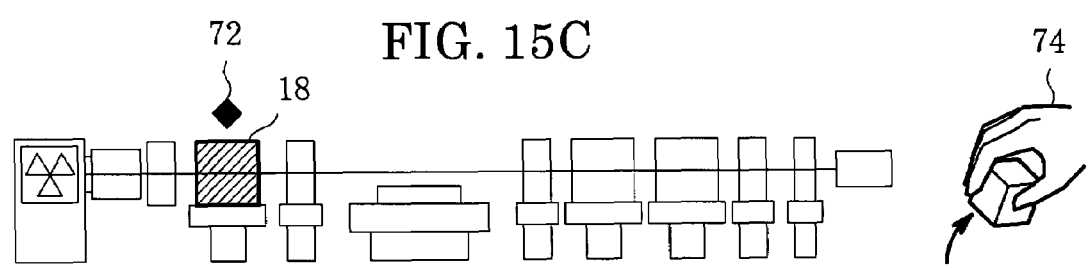

FIG. 15C shows an example indicating how to instruct the removal work. The example indicates the removal of the optical part from the category of the incident optical device 18. The location of the incident optical device 18 is highlighted, and the identification mark 72 (the inclined black square mark) peculiar to the category of the incident optical device appears above the highlighted category 18, and further the pictorial expression 74 for the removal work is displayed. The pictorial expression 74 has a picture symbolizing a human hand which removes the optical part from the apparatus.

Turning to the window shown FIGS. 14A and 14B, there will be explained the operation instructions window regarding the change of the optical part. Referring to FIG. 14A, instructions with a sentence "Place the height reference sample plate on the attachment." are displayed at the top of the window. Further, the picture of the height reference sample plate is also displayed. In accordance with the instructions, the operator places the height reference sample plate on the attachment of the sample stage.

Next, instructions with sentences "Insert selection slit PB in CBO unit." and "→Selection slit BB is currently on CBO unit." are displayed, and the content of the instructions is graphically displayed. Namely, the location of the CBO selection slit 16 is highlighted, and the identification mark 70 (the black circle mark) peculiar to the CBO selection slit appears above the highlighted category 16, and further the pictorial expression 69 for the installation work is displayed at the rightmost region for indicating the type of work. The operator looks at the information and understands that the selection slit BB should be removed from the CBO unit 24 (see FIG. 1A) of the X-ray analysis apparatus and the selection slit PB should be inserted. Then, the operator finds out the selection slit PB among the plural optical parts (the four types of the selection slit: BB, PB, SA and MA) which have the black circle marks, and inserts it in the CBO unit. It should be noted that although the replacement work of the optical part consists of a combination of the removal work of the optical part which is currently installed and the installation work of the necessary optical part which should be newly installed, the replacement work may be displayed with one figure of instructions if the instructions are simple, the removal-work pictorial expression 69 being displayed in such a case.

Next, instructions with a sentence "Remove IPS adaptor." are displayed, and the content of the instructions is graphically displayed. "IPS adaptor" suggests the Incident Parallel Slit adaptor. The location of the incident optical device 18 is highlighted, and the identification mark 72 (the inclined black square mark) peculiar to the incident optical device appears above the highlighted category 18, and further the pictorial expression 74 for the removal work is displayed at the rightmost region for indicating the type of work. The operator looks at the information and understands that the incident parallel slit adaptor should be removed from the incident optical device base 26 (see FIG. 1A) of the X-ray analysis apparatus. Then, the operator performs the instructed work.

Similarly, the operator performs other works in accordance with the operating instructions displayed in the window shown in FIGS. 14A and 14B. The other works are: installation of the "2-bounce monochromator Ge(220)×2" in the incident optical device base 26 (see FIG. 1A); installation of the "Soller-slit-open" in the thus installed 2-bounce monochromator; insertion of the "Center slit" in the height reference sample plate; removal of the "DBM unit" (Diffracted Beam Monochromator unit) from the detector adaptor 46 (see FIG. 1A); removal of the "detector" (X-ray detector) from the thus removed DBM unit; and installation of the thus removed "detector" in the detector adaptor 46. Then, the operator clicks the "OK" button.

Then, the X-ray analysis apparatus performs the optics alignment automatically. Since the optics alignment proceeds under the recommended conditions, the operator has nothing to do and waits for the completion of the optics alignment. After the completion of the optics alignment, the operating instructions window shown in FIG. 16 is displayed.

In the operating instructions window shown in FIG. 16, instructions with a sentence "Place the sample spacer (0-3 mm) and the wafer sample plate (standard) on the attachment." are displayed, and the operator places them on the attachment of the sample stage. Further, other instructions with a sentence "Place the sample on the wafer sample plate." are displayed together, and the operator performs such instructions too.

Next, instructions with sentences "Insert length limiting slit 5 (mm) in incident slit box." and "→Length limiting slit 10 (mm) is currently on incident slit box." are displayed, and the content of the instructions is graphically displayed. The operator removes the "Length limiting slit 10 (mm)" from the incident slit box 28 (see FIG. 1A) and installs the "Length limiting slit 5 (mm)" in accordance with the displayed instructions. The replacement of the length limiting slit is for the transition from the optics alignment to the sample alignment. When the operator clicks the "OK" button, the X-ray analysis apparatus performs the sample alignment automatically. Since the sample alignment also proceeds under the recommended conditions, the operator has nothing to do. After the completion of the sample alignment, the X-ray analysis apparatus advances to the data measurement automatically, and then the reflectivity measurement is completed.

Figure 17:
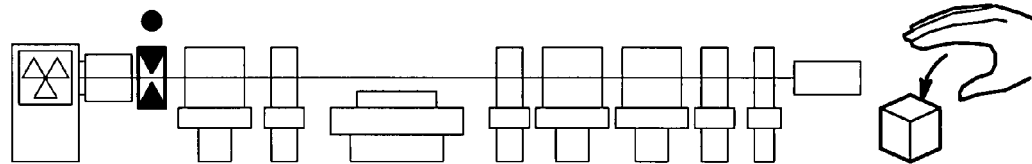
FIG. 17 shows further another operating instructions window.

Next, a certain case in which a wrong optical part is installed will be described. Although the operating instructions window shown FIG. 14A instructs the insertion of the selection slit PB, it is assumed that the operator mistakenly inserts the selection slit SA. In such a case, after the operator clicks the "OK" button shown in FIG. 14B, the X-ray analysis apparatus determines the difference between the installed optical part and the content of the instructions with the use of the output signal of the sensor. Then, the X-ray analysis apparatus displays the operating instructions window shown in FIG. 17 without starting the optics alignment. This window displays the operating instructions for replacing the wrong optical part with the proper optical part. Namely, instructions for replacing the wrong selection slit SA with the proper selection slit PB are displayed with sentences, and the content of the instructions is graphically displayed.

Figure 18:
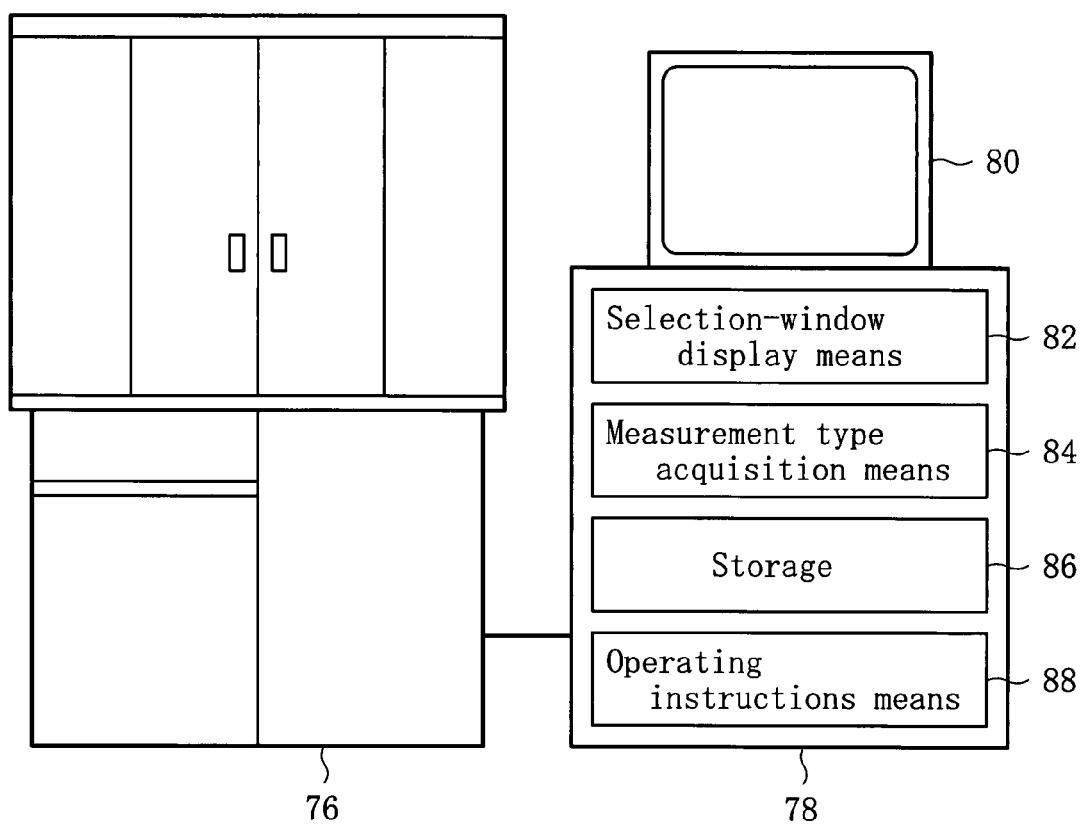
FIG. 18 is a front view illustrating the entire picture of the X-ray analysis apparatus.

Next, the entire structure of the X-ray analysis apparatus will be described. FIG. 18 is a front view illustrating the entire picture of the X-ray analysis apparatus. The X-ray analysis apparatus has a main equipment 76, a control device 78 and a display 80. The main equipment 76 contains the optical system shown in FIG. 1A. The display 80 displays the selection window shown in FIG. 5 and further displays the windows shown in FIGS. 6 to 11, 13, 14A, 14B, 16 and 17 respectively. The control device 78 includes selection-window display means 82, measurement type acquisition means 84, a storage 86 and operating instructions means 88. The selection-window display means 82 is means for realizing the function of displaying the selection window shown in FIG. 5 on the display 80. The measurement type acquisition means 84 is means for realizing the function of acquiring the measurement type which is selected by the operator in the selection window shown in FIG. 5. The storage 86 stores the relationship shown in FIGS. 12A and 12B. The operating instructions means 88 is means for realizing the function of displaying the operating instructions windows shown in FIGS. 13, 14A, 14B, 16 and 17. The selection-window display means 82, the measurement type acquisition means 84 and the operating instructions means 88 are realized by the computer's software.

What is claimed is:

1. An X-ray analysis apparatus comprising:
   (a) a main equipment including an optical system for performing an X-ray analysis of a sample, the optical system comprising an X-ray source, an X-ray detector, and optical parts therebetween that are classified into a plurality of categories so that the optical parts installed in the main equipment are exchangeable with other optical parts belonging to the same category;
   (b) a display for displaying information about the main equipment;
   (c) selection-window display means for causing a selection window to be displayed on the display, the selection window being used for selection of one desired measurement type among a plurality of measurement types;
   (d) measurement type acquisition means for acquiring the measurement type which is selected by an operator in the selection window;
   (e) a storage for storing a relationship between the measurement type and types of necessary optical parts required for the measurement type in connection with the plurality of the measurement types respectively;
   (f) sensors for identifying types of the installed optical parts which have been installed in the main equipment; and
   (g) operating instructions means for:
   acquiring the types of the necessary optical parts corresponding to the measurement type which has been acquired by the measurement type acquisition means in accordance with the relationship which is stored in the storage;
   comparing the types of the necessary optical parts with the types of the installed optical parts which have been identified by the sensors to recognize at least one mismatched optical part; and
   causing graphical information to be displayed on the display in connection with the at least one mismatched optical part, the graphical information including information about at least one of: the necessary optical part which should be newly installed in the main equipment, and the installed optical part which should be removed from the main equipment.

2. The X-ray analysis apparatus according to claim 1, wherein the operating instructions means i) causes at least one of the type of the necessary optical part which should be newly installed in the main equipment and the type of the installed optical part which should be removed from the main equipment to be displayed on the display and ii) causes at least one installation location in the optical system of such at least one optical part to be graphically displayed on the display.

3. The X-ray analysis apparatus according to claim 2, wherein the operating instructions means causes at least one of an installation work of the necessary optical part and a removal work of the installed optical part to be graphically displayed on the display, the installation and the removal works being depicted with different pictorial expressions.

4. The X-ray analysis apparatus according to claim 3, wherein:
   each of the optical parts has an identification mark which identifies the category to which the optical part belongs; and
   the operating instructions means causes the identification mark to be displayed when showing, on the display, at least one of the type of the necessary optical part which should be newly installed in the main equipment and the type of the installed optical part which should be removed from the main equipment.

5. The X-ray analysis apparatus according to claim 1, wherein the operating instructions means causes at least one of an installation work of the necessary optical part and a removal work of the installed optical part to be graphically displayed on the display, the installation and the removal works being depicted with different pictorial expressions.

6. The X-ray analysis apparatus according to claim 5, wherein:
   each of the optical parts has an identification mark which identifies the category to which the optical part belongs; and
   the operating instructions means causes the identification mark to be displayed when showing, on the display, at least one of the type of the necessary optical part which should be newly installed in the main equipment and the type of the installed optical part which should be removed from the main equipment.

7. The X-ray analysis apparatus according to claim 1, wherein:
   each of the optical parts has an identification mark which identifies the category to which the optical part belongs; and
   the operating instructions means allows the identification mark to be displayed when showing, on the display, at least one of the type of the necessary optical part which should be newly installed in the main equipment and the type of the installed optical part which should be removed from the main equipment.

8. A method of instructing an operation of arranging an X-ray analysis apparatus, wherein the X-ray analysis apparatus comprises: (i) a main equipment including an optical system for performing an X-ray analysis of a sample, the optical system comprising an X-ray source, an X-ray detector, and optical parts therebetween that are classified into a plurality of categories so that the optical parts installed in the main equipment are exchangeable with other optical parts belonging to the same category; (ii) a display for displaying information about the main equipment; and (iii) a storage which stores a relationship between a measurement type and types of necessary optical parts required for the measurement type in connection with a plurality of the measurement types respectively, the method comprising:

displaying a selection window on the display, the selection window being used for selection of a desired measurement type among the plurality of the measurement types;

acquiring the measurement type which is selected by an operator in the selection window;

identifying, using sensors, types of the installed optical parts which are installed in the main equipment;

acquiring the types of the necessary optical parts corresponding to the acquired measurement type in accordance with the relationship which is stored in the storage;

comparing the types of the necessary optical parts with the types of the installed optical parts to recognize at least one mismatched optical part; and displaying graphical information on the display in connection with the at least one mismatched optical part, the graphical information including information about at least one of: the necessary optical part which should be newly installed in the main equipment, and the installed optical part which should be removed from the main equipment.

9. The method according to claim 8, wherein displaying the graphical information comprises i) displaying on the display at least one of the type of the necessary optical part which should be newly installed in the main equipment and the type of the installed optical part which should be removed from the main equipment, and ii) graphically displaying on the display at least one installation location in the optical system of such at least one optical part.

10. The method according to claim 9, wherein displaying the graphical information comprises graphically displaying on the display at least one of an installation work of the necessary optical part and a removal work of the installed optical part, the installation and the removal works being depicted with different pictorial expressions.

11. The method according to claim 10, wherein:
each of the optical parts has an identification mark which identifies the category to which the optical part belongs; and displaying the graphical information comprises displaying the identification mark when showing, on the display, at least one of the type of the necessary optical part which should be newly installed in the main equipment and the type of the installed optical part which should be removed from the main equipment.

12. The method according to claim 8, wherein displaying the graphical information comprises graphically displaying on the display at least one of an installation work of the necessary optical part and a removal work of the installed optical part, the installation and the removal works being depicted with different pictorial expressions.

13. The method according to claim 12, wherein:
each of the optical parts has an identification mark which identifies the category to which the optical part belongs; and displaying the graphical information comprises displaying the identification mark when showing, on the display, at least one of the type of the necessary optical part which should be newly installed in the main equipment and the type of the installed optical part which should be removed from the main equipment.

14. The method according to claim 8, wherein:
each of the optical parts has an identification mark which identifies the category to which the optical part belongs; and displaying the graphical information comprises displaying the identification mark when showing, on the display, at least one of the type of the necessary optical part which should be newly installed in the main equipment and the type of the installed optical part which should be removed from the main equipment.

* * * * *